United States Patent
Fermandjian et al.

(10) Patent No.: US 6,562,788 B1
(45) Date of Patent: May 13, 2003

(54) TOPOISOMERASE II INHIBITOR

(75) Inventors: Serge Fermandjian, Meudon (FR); Valérie Frere-Gallois, Ivry sur Seine (FR); Frédéric Troalen, Bourg la Reine (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/868,864

(22) PCT Filed: Dec. 20, 1999

(86) PCT No.: PCT/FR99/03208

§ 371 (c)(1),
(2), (4) Date: Jun. 21, 2001

(87) PCT Pub. No.: WO00/37499

PCT Pub. Date: Jun. 29, 2000

(30) Foreign Application Priority Data

Dec. 22, 1998 (FR) .............................. 98 16264

(51) Int. Cl.⁷ .................. A61K 38/00; C07K 14/00

(52) U.S. Cl. ......................... 514/12; 530/324

(58) Field of Search ................. 530/300, 350; 514/1, 2, 12; 536/23.1

(56) References Cited

PUBLICATIONS

Graddis, Tom; Chaiken, Irwin. Designing homodimers and heterodimers with sequence simplified leucine zipper models. Pept.: Chem. Biol., Proc. Am. Pept. Symp., 12th (1992), Meeting Date 1991, 360–1. Editor(s): Smith, John A.; Rivier, Jean E.*

Frere–Gallois V, Krebs D, Scala D, Troalen F, Fermandjian S. Peptide fragments of DNA topoisomerase II with helix–forming and coiled–coil–forming properties act as inhibitors of the enzyme. Eur J Biochem. Oct. 1, 1997; 249(1):142–8.*

Kohn WD, Monera OD, Kay CM, Hodges RS. The effects of interhelical electrostatic repulsions between glutamic acid residues in controlling the dimerization and stability of two–stranded alpha–helical coiled–coils. J Biol Chem. Oct. 27, 1995;2.*

Frere V, Sourgen F, Monnot M, Troalen F, Fermandjian S. A peptide fragment of human DNA topoisomerase II alpha forms a stable coiled–coil structure in solution. J Biol Chem. Jul. 21, 1995;270(29):17502–7.*

XP–002121994, Frere–Gallois et al., "Peptide Fragments of DNA Topoisomerase II with Helix–Forming and Coiled–Coil–Forming Properties Act as Inhibitors of the Enzyme", 08–97, pp. 142–148.

XP–002121995, Gudkov et al., "Isolation of Genectic Suppressor Elements, Inducing Resistance to Topoisomerase II–Interactive Cytotoxic Drugs, from Human Topoisomerase II cDNA", 01–93, pp. 3231–3235.

XP–002121996, Kroll, "Homologous and Heterologous Protein–Protein Interactions of Human DNA Topoisomeras 11α", 06–97, pp. 175–184.

XP–002121997, Grigolo et al. "Mapping of Topoisomeras II α Epitopes Recognized by Autoantibodies in Idiopathic Pulmonary Fibrosis", 09–98, pp. 339–346.

XP–002121998, Biersack et al. "DNA Topoisomerase IIα/β Heterodimers Might Serve as a New Target for Topoisomerase Targeting Drugs", 1997, p. 1030.

XP–004143168, Lang et al., "Structural Organization of the Human Top2A AD Top2B Genes", 08–98, pp. 255–266.

* cited by examiner

Primary Examiner—Karen Cochrane Carlson
Assistant Examiner—Sheridan K Snedden
(74) Attorney, Agent, or Firm—Young & Thompson

(57) ABSTRACT

A peptide having the following amino acid sequence:

```
Thr-X₁-Leu-Asp-Ile-X₂-X₃-Asp-Leu-X₄-Glu-X₅-
         5                        10

Arg-Leu-Lys-Tyr-Tyr-X₆-X₇-Arg-Lys-Glu-Phe-Leu-X₈-
       15              20                    25

X₉-X₁₀-Leu-Gly
```

(SEQ ID NO: 1) wherein $X_1$=Gln or Glu; $X_2$=Leu or Lys; $X_3$=Arg or Lys; $X_4$=Phe or Tyr; $X_5$=Leu or Lys; $X_6$=Gly or Glu; $X_7$=Leu or Glu; $X_8$=Leu or Glu; $X_9$=Gln or Lys; $X_{10}$=Met or Nle; and its pharmaceutically acceptable protected derivatives. The peptides are useful in therapy, in particular antitumoral therapy.

8 Claims, No Drawings

SEQUENCE LISTING

```
<160> NUMBER OF SEQ ID NOS: 2

<210> SEQ ID NO 1
<211> LENGTH: 29
<212> TYPE: PRT
<213> ORGANISM: Artificial Sequence
<220> FEATURE:
<221> NAME/KEY: MOD_RES
<222> LOCATION: (2)
<223> OTHER INFORMATION: Gln or Glu
<221> NAME/KEY: MOD_RES
<222> LOCATION: (6)
<223> OTHER INFORMATION: Leu or Lys
<221> NAME/KEY: MOD_RES
<222> LOCATION: (7)
<223> OTHER INFORMATION: Arg or Lys
<221> NAME/KEY: MOD_RES
<222> LOCATION: (10)
<223> OTHER INFORMATION: Phe or Tyr
<221> NAME/KEY: MOD_RES
<222> LOCATION: (12)
<223> OTHER INFORMATION: Leu or Lys
<221> NAME/KEY: MOD_RES
<222> LOCATION: (18)
<223> OTHER INFORMATION: Gly or Glu
<221> NAME/KEY: MOD_RES
<222> LOCATION: (19)
<223> OTHER INFORMATION: Leu or Glu
<221> NAME/KEY: MOD_RES
<222> LOCATION: (25)
<223> OTHER INFORMATION: Leu or Glu
<221> NAME/KEY: MOD_RES
<222> LOCATION: (26)
<223> OTHER INFORMATION: Gln or Lys
<221> NAME/KEY: MOD_RES
<222> LOCATION: (27)
```

-continued

```
<223> OTHER INFORMATION: Met or Nle
<223> OTHER INFORMATION: Description of Artificial Sequence: Synthetic
      peptide

<400> SEQUENCE: 1

Thr Xaa Leu Asp Ile Xaa Xaa Asp Leu Xaa Glu Xaa Arg Leu Lys Tyr
 1               5                  10                  15

Tyr Xaa Xaa Arg Lys Glu Phe Leu Xaa Xaa Xaa Leu Gly
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Gln Leu Asp Ile Leu Arg Asp Leu Phe Glu Leu Arg Leu Lys Tyr
 1               5                  10                  15

Tyr Gly Leu Arg Lys Glu Phe Leu Leu Gln Met Leu Gly
            20                  25
```

TOPOISOMERASE II INHIBITOR

CROSS-REFERENCE

This application is a national stage of PCT/FR99/03208, filed Dec. 22, 1999, which claims priority to French application 98/16264 filed Dec. 22, 1998.

The present invention relates to peptides which have strong inhibitory activity for human topoisomerase II alpha, and which find an application in therapeutics, in particular as antitumor agents.

DNA topoisomerase II is an enzyme which is essential to the life of eukaryotic cells. It changes the topology of the DNA by transient double-stranded cleavage of a DNA double helix, through which it passes another DNA helix. In addition to the biological advantage of this enzyme, there is a pharmacological advantage, since it is the preferred target of many antitumor agents (Corbett and Osheroff, Chem. Res. Toxicol., 6, 585, 1993).

One of the major problems of current anticancer chemotherapy consists of the lack of specificity of the antitumor agents targeting topoisomerase II. In order to resolve this problem, we have developed a novel class of peptide inhibitors of topoisomerase II, which interact selectively with this enzyme and block its catalytic activity.

Frére Gallois et al. have described, in Eur. J. Biochem., 249, 142, 1997, a topoisomerase II fragment, corresponding to sequence 1013 to 1041 of human topoisomerase II alpha which has inhibitory activity for topoisomerase II.

The present invention is directed toward providing peptides which have greater inhibitory activity.

A subject of the present invention is thus a peptide having the following amino acid sequence:

(SEQ ID NO: 1)
Thr-$X_1$-Leu-Asp-Ile-$X_2$-$X_3$-Asp-Leu-$X_4$-Glu-$X_5$-
                 5                         10
Arg-Leu-Lys-Tyr-Tyr-$X_6$-$X_7$-Arg-Lys-Glu-Phe-Leu-$X_8$-
      15                  20                    25
$X_9$-$X_{10}$-Leu-Gly.

The expression "pharmaceutically acceptable protected derivative" is intended to mean, in particular, derivatives comprising pharmaceutically acceptable N-protective groups.

Pharmaceutically acceptable N-protective groups are, in particular, the groups which protect against N-terminal attack by exopeptidase enzymes. As examples of such groups, mention may be made of acyl groups, such as t-butyloxycarbonyl (Boc), tert-amyloxycarbonyl ($^+$Aoc), benzyloxycarbonyl, benzoyl, acetyl, formyl, propanoyl, butanoyl, phenylacetyl, phenylpropanoyl or cyclo pentylcarbonyl groups.

The peptides according to the invention can be prepared conventionally by peptide synthesis in liquid or solid phase, by successive coupling of the various amino acid residues which have to be incorporated (from the N-terminal end toward the C-terminal end in liquid phase, or from the C-terminal end toward the N-terminal end in solid phase), and the N-terminal ends and reactive side chains of which have been blocked beforehand.

As examples of groups which block the N-terminal ends, mention may be made of: Boc, Bpoc, Fmoc.

A subject of the present invention is also a pharmaceutical composition comprising, as an active ingredient, a peptide according to the invention.

Such compositions can be used as an antiviral, antibacterial, antiparasitic or anticancer agent, such as for example in the treatment of tumors or of parasitic diseases, leishmaniasis or Chagas disease, or in the treatment of respiratory tract diseases, such as otitis or pneumonias.

Prior vectorization of the peptide may prove to be advantageous since it may promote contact between the peptide and the target cells. The methods of vectorization are known to those skilled in the art. One of these methods consists in encapsulating the peptide in liposomes, such as cationic liposomes. It is known that these liposomes ensure additional protection of the peptide against degradation in vivo. Thus, the slow release of the active ingredient in the targeted areas is therefore very clearly promoted. The first step of the process of transfecting the targeted cells with the peptide, or of the process of peptide release, involves the formation of a complex between the lipid wall of the liposome and the peptide.

After fusion of the respective membranes of the liposome and of the cell, the peptide is released into the cytoplasm.

The preparation of such liposomes is described in detail in "Liposome technology", Gregoriadis (CFC Press, NY 1984), in "Liposomes", Ostro (Macel Dekker, 1987) or in the publication by Lichtenberg et al., which appeared in "Methods Biochem. Anal. 33: 337–462, 1988". In the liposomes, the peptide is either dispersed, contained or otherwise trapped, in corpuscles consisting of concentric aqueous layers adhering to lipid layers. The peptide is either contained in the aqueous phase or contained in the lipid phase, and optionally in each of the two phases, depending on its solubility. The lipid phase can, in particular, comprise phospholipids such as lecithin or sphingomyelin, steroids such as cholesterol, surfactants such as decetyl phosphate, stearylamine or phosphatidic acid, and/or other hydrophobic materials. The diameter of the liposomes preferably varies between 15 nm and 5 $\mu$m.

It is also possible to envision vectorization by incorporating the peptide into biodegradable microspheres.

The preparation of the compositions of the invention is carried out conventionally and depends on the method of administration envisioned.

According to a preferred embodiment of the invention, the peptides optionally incorporated into a vector are administered transdermally, transmucosally or intratumorally. The compositions of the invention are preferably in the form of injectable solutions or suspensions.

As a pharmaceutically acceptable vehicle, use will be made essentially of buffers, a phosphate buffered saline solution (PBS) ,or any other solution provided that it has a physiologically acceptable pH.

The active ingredient can also be incorporated into a matrix or a vehicle in the form of hydrated gel, for example a gel based on a propylene oxide/ethylene oxide copolymer, which is liquid below room temperature and gelatinous at a temperature equal to or higher than room temperature. Before administration, the gel can optionally be fluidized.

In order to enable delayed release of the active ingredient, it is possible, as a variant, to formulate the peptide in a sustained-release composition. Such compositions have been described in the literature. To this end, the peptide can in particular be combined with polylactic acid polymers.

All these compositions can be applied locally by direct injection, or released from implants, or diffused locally using a suitable pump.

A subject of the present invention is also a method for treating a patient with a tumor, which comprises the administration, to this patient, of an effective amount of a peptide according to the invention.

The amount of peptide to be administered depends on the cancerous pathological condition of the individual to be treated, on the seriousness (presence or absence of metastases) of the disease, on the chemotherapy protocol selected, on the choice of a first or second line treatment and on the duration of the treatment, and also on the general condition of the patient. The daily doses can be between 0.1 mg/kg and 10 mg/kg per day or per week, depending on the number of treatment cycles for each therapy.

EXAMPLE 1

Peptide having the sequence

Thr-Gin-Leu-Asp-Ile-Leu-Arg-Asp-Leu-Phe-Glu-Leu-Arg -Leu-Lys-Tyr-Tyr-Gly-Leu-Arg-Lys-Glu-Phe-Leu-Leu-Gin-Met -Leu-Gly (SEQ ID NO: 2).

The synthesis of the corresponding peptide was carried out by solid phase chemical process according to the Fmoc (9-fluorenylmethoxycarbonyl) strategy, on an Applied Biosystem 432 A automatic synthesizer using an HMP resin (4-hydroxymethyl)phenoxymethyl-copoly-(styrene-1% divinylbenzene)) and activation with HBTU (2-(1H-benzotriazol-1-yl)-1,1,3,3-tetraethyluronium hexafluorophosphate). The N- and C-terminal ends were left free. The deprotection was carried out with TFA (trifluoroacetic acid). The deprotected peptide was then filtered in order to separate it from the resin, and precipitated in cold ether. The peptide was purified by reverse phase HPLC with a Beckman Gold System machine on a Spherisorb $C_{18}$ column (25×1 cm, 2 $\mu$m and 300 Å), with a linear gradient of 0 to 100% of acetonitrile/water (with 0.1% of TFA) over 45 minutes, the flow rate being 4 ml/min. The fractions simultaneously exhibiting maximum absorption peaks at 220 and 274 nm are subsequently characterized by analytical HPLC, and the fractions containing the pure peptide are pooled and lyophilized.

The peptide after purification was characterized by:

reverse phase analytical HPLC with a Nucleosyl $C_{18}$ column (25×0.46 cm, 5 $\mu$m and 300 Å) using an acetonitrile/water gradient (with 0.1% of TFA) over 45 minutes with a flow rate of 1 ml/min;

analysis of the amino acid composition using a Beckman AAA-6300 machine;

sequencing on an Applied Biosystem 477 A machine, using the Edman degradation method;

mass spectroscopy (ESIMS) on a VG Biotech quadrupole instrument.

INHIBITION OF TOPOISOMERASE II

Activity assay

Two enzymatic assays make it possible to estimate the effect of the pentides on topoisomerase II activity: relaxation of supercoiled plasmids and decatenation of kinetoplast DNA (Wang, J. C., An. Rev. Biochem., 54: 665–697, 1985; Maxwell, A., Advances in Protein Chemistry, 38: 69–107, 1986; Liu, L. F., Cell, 19: 697–707, 1980). The peptide of example 1 totally inhibits the activity of human topoisomerase II alpha and that of yeast, in both assays, at a concentration of 0.5 $\mu$M.

What is claimed is:

1. A peptide having the following amino acid sequence:

Thr-$X_1$-Leu-Asp-Ile-$X_2$-$X_3$-Asp-Leu-$X_4$-Glu-$X_5$-
                      5                 10

Arg-Leu-Lys-Tyr-Tyr-$X_6$-$X_7$-Arg-Lys-Glu-Phe-Leu-$X_8$-
       15              20            25

$X_9$-$X_{10}$-Leu-Gly (SEQ ID NO: 1) in which:
   $X_1$=Gln or Glu
   $X_2$=Leu or Lys
   $X_3$=Arg or Lys
   $X_4$=Phe or Tyr
   $X_5$=Leu or Lys
   $X_6$=Gly or Glu
   $X_7$=Leu or Glu
   $X_8$=Leu or Glu
   $X_9$=Gln or Lys
   $X_{10}$=Met or Nle, and the pharmaceutically acceptable protected derivatives thereof.

2. The peptide as claimed in claim 1, having the following amino acid sequence:

Thr-Gln-Leu-Asp-Ile-Leu-Arg-Asp-Leu-Phe-Glu-Leu-Arg-Leu-Lys-Tyr-Tyr-Gly-Leu-Arg-Lys-Glu-Phe-Leu-Leu-Gln-Met-Leu-Gly (SEQ ID NO: 2).

3. A composition comprising, as an active ingredient, a peptide as claimed in claim 1.

4. A composition having inhibitory activity for human topoisomerase II alpha, comprising, as an active ingredient, a peptide as claimed in claim 1.

5. A method for treating a patient with a tumor, comprising administering to said patient an effective amount of a peptide as claimed in claim 1 for the treatment of said patient.

6. A composition comprising, as an active ingredient, a peptide as claimed in claim 2.

7. A composition having inhibitory activity for human topoisomerase II alpha, comprising, as an active ingredient, a peptide as claimed in claim 2.

8. A method for treating a patient with a tumor, comprising administering to said patient an effective amount of a peptide as claimed in claim 2 for the treatment of said patient.

* * * * *